United States Patent
Chelle

(10) Patent No.: US 9,060,520 B2
(45) Date of Patent: Jun. 23, 2015

(54) DOMESTIC ANIMAL PARASITE-REPELLENT DEVICE

(75) Inventor: René Chelle, Grepiac (FR)

(73) Assignee: AB7 INNOVATION, Deyme (FR)

( * ) Notice: Subject to any disclaimer, the term of this patent is extended or adjusted under 35 U.S.C. 154(b) by 549 days.

(21) Appl. No.: 12/681,310

(22) PCT Filed: Oct. 2, 2008

(86) PCT No.: PCT/FR2008/001382
§ 371 (c)(1),
(2), (4) Date: Apr. 1, 2010

(87) PCT Pub. No.: WO2009/080909
PCT Pub. Date: Jul. 2, 2009

(65) Prior Publication Data
US 2010/0226952 A1   Sep. 9, 2010

(30) Foreign Application Priority Data
Oct. 2, 2007   (FR) ...................... 07 06888

(51) Int. Cl.
*A01N 25/08*   (2006.01)
*A01K 27/00*   (2006.01)
*A01N 53/00*   (2006.01)
*A01N 57/16*   (2006.01)
*A01N 65/00*   (2009.01)

(52) U.S. Cl.
CPC ............... *A01N 53/00* (2013.01); *A01N 57/16* (2013.01); *A01N 65/00* (2013.01)

(58) Field of Classification Search
USPC ........................................ 424/411
See application file for complete search history.

(56) References Cited

U.S. PATENT DOCUMENTS

| 4,166,111 A | 8/1979 | Cardarelli |
| 4,228,614 A | 10/1980 | Cardarelli |
| 4,237,113 A | 12/1980 | Cardarelli |
| 4,830,860 A * | 5/1989 | Ranade ................. 424/486 |

(Continued)

FOREIGN PATENT DOCUMENTS

| EP | 0152190 A1 | 8/1985 |
| EP | 0194934 A1 | 9/1986 |
| EP | 0537998 A1 | 4/1993 |

(Continued)

OTHER PUBLICATIONS

Aki et al., "Resin Mouldings Gradually Releasing Insecticide—Prepd. by Mixing 1-Ethynyl-2-Methyl-2-Pentenyl Chrysanthemate with Synthetic Resin and Thermo-Forming Into Sheet", Sep. 2, 1991, XP002418473.

(Continued)

*Primary Examiner* — Michael B Pallay
(74) *Attorney, Agent, or Firm* — Birch, Stewart, Kolasch & Birch, LLP

(57) ABSTRACT

The present invention comprises a device for storing and releasing one or more mixed active compositions, for intensively controlling the external parasites of domestic animals, insects and other undesirable living organisms, composed of a polymer matrix comprising an ethylene/vinyl acetate copolymer blended with a polyether block amide, said polymer matrix being charged in an active composition/matrix ratio by weight of less than 0.66. A method for manufacturing such a device is also claimed.

13 Claims, 11 Drawing Sheets

(56) References Cited

U.S. PATENT DOCUMENTS 5,310,557 A * 5/1994 Brandt et al. ............... 424/411
2003/0198659 A1 10/2003 Hoffmann et al.

FOREIGN PATENT DOCUMENTS

| EP | 0542080 A1 | 5/1993 |
|----|------------|--------|
| FR | 2745720 A1 | 9/1997 |
| FR | 2781336 A1 | 1/2000 |
| FR | 2901096 A1 | 11/2007 |
| GB | 2276171 A | 9/1994 |
| WO | WO 90/14107 A1 | 11/1990 |
| WO | WO 98/34479 A1 | 8/1998 |
| WO | WO 0035277 A1 | 6/2000 |
| WO | WO 01/49331 A2 | 7/2001 |
| WO | WO 01/65937 A1 | 9/2001 |
| WO | WO 2004/086862 A2 | 10/2004 |
| WO | WO 2006/105572 A1 | 10/2006 |
| ZA | 981019 | 8/1998 |

OTHER PUBLICATIONS

Chinuki et al., "Harmful Insect-Evading Resin Moulding—Obtd. by Combining Essential Oil White Cedar in a Synthetic Resin Moulding Allowing a Slow Release of Medicines and Reduces the Presence of Harmful Insects, e.g., cockroaches", Jul. 22, 1992, XP002418472.

Numamoto et al., "Prodn. of Film Contg. Volatile Agent for Sustained Release—by Coextruding Polymer Contg. the Volatile Agent, Polymer Functioning as Barrier and Permeable Polymer", Feb. 9, 1984, WPI/Thompson, XP002418474.

* cited by examiner

DOMESTIC ANIMAL PARASITE-REPELLENT DEVICE

The object of the present invention is a novel device for storing and releasing with differential kinetics one or more mixed active compositions for intensively controlling the external parasites of domestic animals, insects and other undesirable living organisms. The device according to the invention is developed from a matrix comprising a mixture of an Ethylene/Vinyl Acetate (EVA) copolymer with PEBAX (Polyether Block Amide), applied to the body, so that the device object of the invention may be described as "fit-on".

Conventionally, the curative treatment of the infestation of domestic animals by external parasites or other undesirable living organisms entails the use, in one or more applications, of an antiparasitic product formulated in the form of shampoos, powders, aerosol lotions or else in the form of a concentrated solution to be applied to a single spot of the epidermis ("spot-on") or along a line, generally the dorsal line ("pour-on").

Shampoos, powders or lotions are "knockdown" treatments but they only have a low remanence, of the order of a few hours. Concentrated solutions, of "spot-on" or "pour-on" type have, in addition to a "knockdown" effect, a long-acting effect that can last up to several days.

Treatments by concentrated solution known as "spot-on" or "pour-on" consist in depositing on the skin a quite significant amount of active ingredient or active composition, viz. a formulated composition containing several active molecules known as active ingredients. Said active composition is formulated so as to favor its dissolution in the sebum, the lipidic layer covering the skin. The sebum ensures the diffusion of the active ingredients over the whole body of the animal. The sebum, and to a certain extent the sebaceous glands, also play the role of reservoir ensuring the remanence of the device. The diffusion in the sebum makes it possible to only have to deposit the product on a limited surface of the tegument, in general on an area that the animal cannot scratch, or lick.

Several brands of spot-on are currently available on the market such as:
  Equi-Spot™ Spot-on for the control of flies for horses,
  Melaflon flea & parasite repellent drops,
  Mowgli insect repellent pipettes,
  Frontline® Spot-on from Merial Laboratories,
  Tiguvon® from Bayer Laboratories.

This mode of treatment is not without several drawbacks:
  the dose is delivered in one shot, which may pose a problem of toxicity;
  the active ingredient deposited is degraded more or less rapidly, the effect drops rapidly over time and the protection becomes virtually nonexistent after a few days;
  some of the active composition is lost through evaporation;
  the animal cannot be washed without leaching out, at the same time, the active composition still on its body;
  even if the product is inaccessible for the animal itself, a non-negligible risk remains for its owners—especially if the dose is delivered on the most stroked part of the animal—as well as for other animals, if the treated subject lives in a group;
  through degradation and through "wear" of the seborrheic film, the concentration of active ingredient progressively diminishes, necessitating high initial overdosing so as to compensate for this loss. Quite logically, the product has to be renewed as soon as the residual dose in the sebum drops below the therapeutic dose. The period during which the animal is carrying a really suitable dose is thus very brief;
  obviously, the doses delivered in one shot cannot be increased indefinitely, at the risk of harming the animal and its masters. The remanence of these systems is thus necessarily limited.

Although the abovementioned products are especially intended for curative treatment, a number of devices aim at ensuring a preventive protection against infestations. The most widespread devices in this category are antiparasitic collars, hereafter called "conventional antiparasitic collars".

Conventional antiparasitic collars are devices that deliver a low amount of active ingredient although in a constant manner and extended over time. Since the storage capacities are important with regard to what is released on a daily basis, it is possible to obtain remanences of the order of several weeks, or even several months.

Conventional antiparasitic collars generally comprise a matrix made of PVC or of EVA alone in which is incorporated the antiparasitic active ingredient according to a very low active composition/matrix ratio.

A very slight peak release effect may be observed on such collar devices the first days of application. This is generally considered as a drawback since it represents a loss of active composition without really enabling a significant effect with regard to antiparasitic action to be obtained. Despite this undesired release, it cannot be considered that there is a real knockdown effect, since the doses released are not high enough; there is no therapeutic knockdown action obtained in the case of the abovementioned curative treatments. To date, laboratories have thus rather sought to limit this phenomenon, assimilated to a loss, as much as possible. The real effect of collar devices is only obtained after several days after their being placed on the animal and extends over time, for several weeks.

In an unexpected manner, unlike the conventional approach of laboratories manufacturing such antiparasitic devices with remanent effect, the present invention is based on the accentuation of the small peak effect observed naturally with the aim of obtaining a real knockdown effect as of the first hours of use of the collar. This knockdown effect makes it possible to obtain a real therapeutic action, which is going to be relayed over time by the remanent diffusion of the active compositions inherent to conventional antiparasitic collars.

The present invention thus aims at providing a solution to the drawbacks of the prior art thanks to a novel device for storing and releasing with differential kinetics one or more mixed active compositions for intensively controlling the external parasites of domestic animals, developed with a matrix comprising Ethylene/Vinyl Acetate copolymer (EVA) blended with a PEBAX (Polyether Block Polyamide). In a wider sense, it will be understood in the course of the present application that the action of the device object of the invention is not limited to controlling external parasites of domestic animals, but also relates to insects and other undesirable living organisms. The "fit-on" according to the invention has, like concentrated liquid forms ("spot-on" and "pour-on"), a curative "knockdown" effect that conventional antiparasitic collars do not have, as well as a prolonged preventive effect over time but without the drawbacks specific to concentrated liquid forms. The EVA/PEBAX mixture according to the invention makes it possible to deliver the active ingredients more quickly if EVA>PEBAX and less quickly and for a longer period if EVA<PEBAX.

According to a first aspect of the invention, there is provided a device for storing and releasing with differential kinetics one or more mixed active antiparasitic compositions, which can act according to complementary spectrums and efficacy periods. Said device is developed with a matrix comprising a mixture of Ethylene/Vinyl Acetate copolymer (EVA) with PEBAX, capable of releasing all of the stored substance.

The antiparasitic control device according to the invention combines the advantages of "spot-on" type concentrated liquid forms and those of conventional antiparasitic collars, offering the capacity to store and release the dose adapted to each active composition.

The abovementioned aims are achieved through the use of a copolymer of ethylene and vinyl acetate (EVA) blended with a PEBAX, to form the matrix in which the antiparasitic ingredients are incorporated and stored, said matrix thus charged being implemented into the requisite form by extrusion or injection molding.

More precisely, according to the invention, there is provided a device for applying anti-parasitic ingredients, it being recalled that the action of the active ingredient(s) is not limited only to parasites, comprising a polymer matrix charged with antiparasitic ingredients wherein said antiparasitic ingredients are incorporated according to the following steps:
 a) choosing the antiparasitic ingredients as a function both of their individual and synergic spectrums in the case where there are several of them and formulating them into antiparasitic compositions;
 b) incorporating the liquid antiparasitic compositions in granules of EVA/PEBAX, heated to suitable temperature for this purpose, in principle below 65° C., preferably at 63° C., according to an active composition/matrix weight ratio below 0.66;
 c) according to the invention, the device for applying antiparasitic ingredients is prepared from granules of EVA/PEBAX, charged with these antiparasitic compositions, the method consisting in an extrusion or injection molding of the granules obtained in step (b).

The final device has a form adapted to its means of application, i.e. either fixation to a collar or any other support so as to contact intimately the hair coat and the skin of the animal, said support being made for example of leather, fabric or plastic material; or in any other suitable form to ensure an intimate contact between the device object of the invention and the hair coat of the animal, such as for example a collar of the same form as a conventional antiparasitic collar.

In this device, the antiparasitic ingredients are dispersed in organic phase by using a vegetable oil—such as evening primrose oil, macadamia oil, sweet almond oil, coconut oil, etc.—as intra-matricial diffusion vector for the antiparasitic ingredients.

The oil, correctly chosen, is a demulcent also intended to prevent any skin irritation. It is also an emollient that enables the passage of the dermal barrier and the transfer to the adipose system, which absorbs the active ingredients, without the sebum being a hindrance and without any other permeation agent. The operation of the device thus takes place in passive diffusion obeying Fick's law:

$$J=(Km \times Dm/E) \times S \times \Delta C$$

with J: flow of active ingredient ($\mu g/cm^2/h$),
 $\Delta C$: concentration difference on either side of the membrane,
 Km: stratum corneum/vehicle partition coefficient,
 Dm: diffusion coefficient ($cm^2/S$),
 S: application surface area ($cm^2$), and
 E: thickness of the corneal layer ($\mu m$).

The rate of transfer of the antiparasitic compositions depends on several factors, which are:
 the nature of the components of the antiparasitic ingredients,
 the volume of antiparasitic ingredients in relation to the volume of the matrix,
 the conditions for obtaining the final device,
 the nature of the components of the matrix,
 the thickness of the final device,
 the rate of dissolution of the active principle in the sebum.

The dissolution in the sebum is of the same nature as spot-on type concentrated liquid formulas as previously mentioned.

The sebum ensures the diffusion of the active principle over the whole surface of the skin. The sebum and the sebaceous glands also ensure a function of storage of the active principle, which is not essential for the operation of the device, unlike what happens for concentrated liquid forms. This storage in the sebum and the sebaceous glands is however worthwhile in that it has a role of regulating the flows of active ingredient.

The operation of the device object of the invention is characterized in that it takes place in two distinct phases:
 (i) a first phase of high release of antiparasitic ingredients that can last up to three days, allowing to reach rapidly the therapeutic concentration (expressed in $mg/m^2$) of the active ingredient in the sebum, without however reaching the extreme concentrations as observed during the use of conventional concentrated liquid formulas, thanks to an active composition/matrix weight ratio lower than 0.66, i.e. up to three times higher than for a conventional antiparasitic collar. Such higher ratio determines the very operation of the device:
 Indeed, the higher this ratio, the higher the internal pressure;
 This pressure will itself determine the force and the release rate of the active ingredients;
 The nature of the matrix considerably influences the release rate. In a specific embodiment example of the invention, the EVA and the PEBAX that constitute the matrix are polymers plastified at "low temperature" and without plasticizier, between 95 and 120° C., which consequently allows to keep undamaged the porous micro-network of the matrix promoting a rapid transfer of the active ingredient from the core of the matrix to the surface, where it is made available. This phenomenon is, by way of comparison, different in the case of a PVC collar, which is necessarily plastified with plasticizers at "high temperature", between 140 and 170° C., which compromises the quality of the porous network and slows down the migration of the active ingredient. To accelerate the migration in this case, a transfer agent that is compatible with the incorporated active ingredients has to be added to the formulation. Collars constituted uniquely of EVA do not enable the double effect, both knockdown and delayed response, claimed in the present application to be obtained. Only a knockdown effect is observed with this type of collar and no extended diffusion over time takes over after the rapid release of the active compositions. There can be no synergy of action;
 The low thickness of the object of the invention, i.e. 2 to 10 mm, preferably 2.5 mm, shortens the path of the active ingredient to the release surface, which represents an important transfer time saving, thus also a higher and more regular flow of active ingredients;

The release of the active ingredients by the object of the invention will be higher and the rate quicker than in the case of a conventional antiparasitic collar for example;

The amount of active ingredients released over a short time by the present invention will be greater than that released over the same time by a conventional antiparasitic collar.

(ii) After the release by the device object of the invention of a large amount of active ingredients, the internal pressure drops considerably, reducing the rate of availability and the flow of said active ingredients, leading to a second phase of decreasing moderate release of antiparasitic ingredients over at least seven days, allowing to compensate the loss due to wear of the lipidic film and the degradation of the active ingredient in the body of the animal.

The device according to the invention thus allow to reach rapidly the therapeutic dose and to maintain said dose over a much longer duration than conventional systems, although using a lower total amount of active ingredients. Moreover, the active composition stored in the matrix according to the invention is not mobilized and thus does not incur any toxic risk for the animal and its masters. It is also protected from degradations (oxidations) which may occur in the case of the use of a concentrated solution deposited directly onto the skin of the animal, which further extends its duration of action.

GIN2: β-citronellol, nerol, geraniol, tetrahydrogeraniol, coprah and castor oil;

GIN3: geraniol, 1-terpinene-4-ol, γ-terpinene, α-terpinene, α-terpinolene, 1,8-cineole, α-pinene, α-terpineol, symene, aromadendrine and d-limonene.

Figure 3:
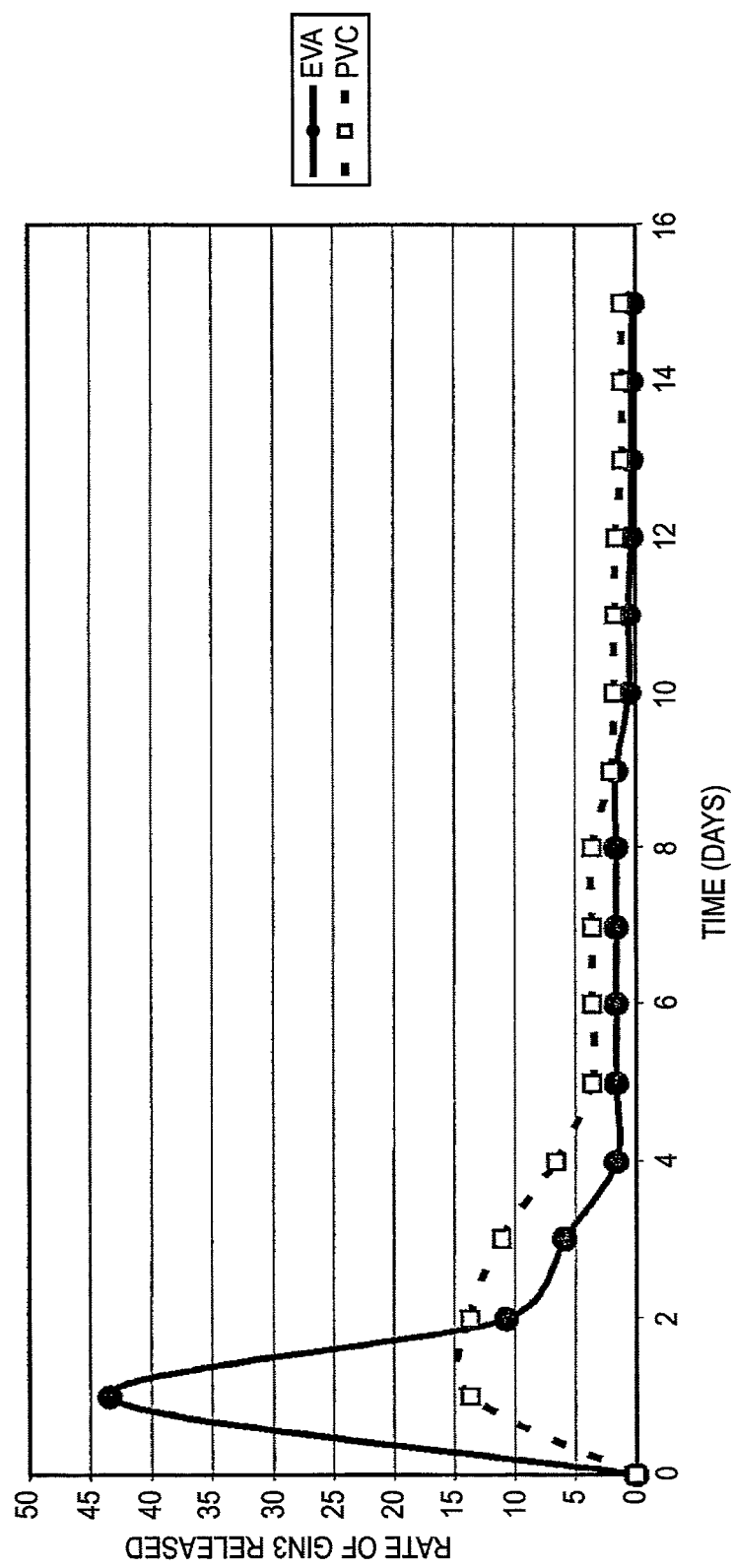

FIG. 3 represents the different kinetic curves of the in vivo operation of an object comprising an EVA matrix, compared to another PVC matrix incorporating the active composition, GIN3.

Figure 4:
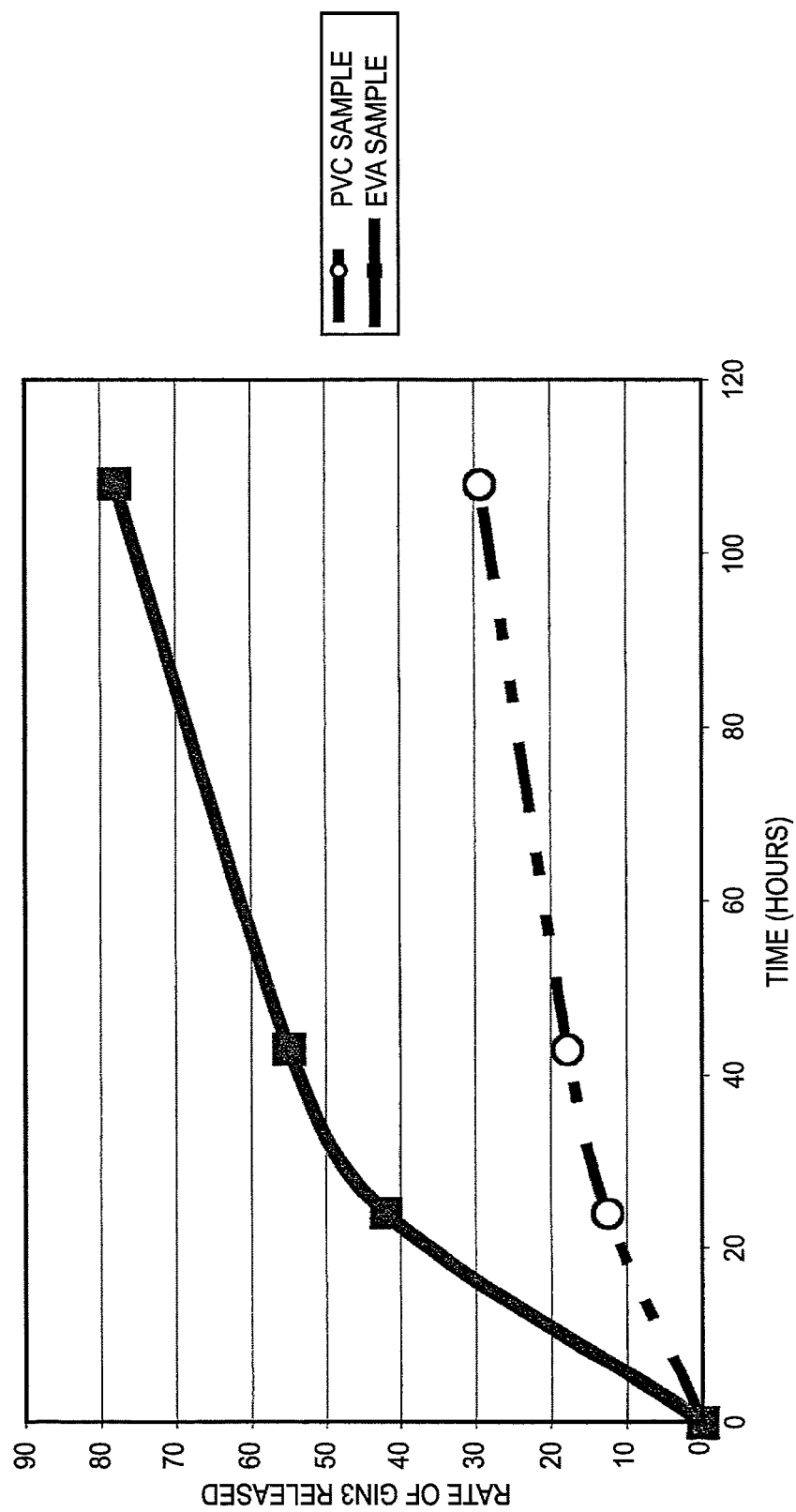

FIG. 4 represents the kinetic curve of the release of GIN3 by an object comprising an EVA matrix applied to a "German shepherd" dog.

Figure 5:
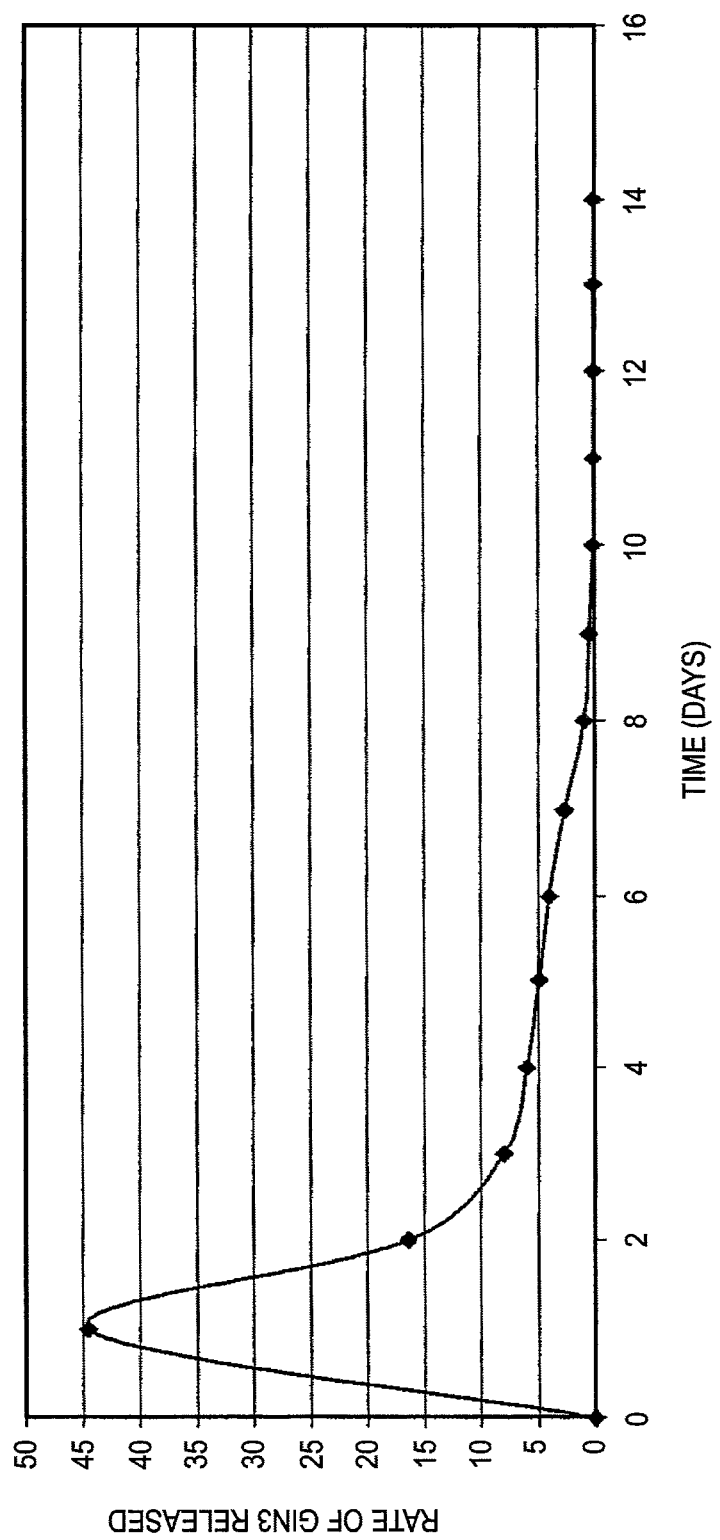

FIG. 5 represents the GIN3 release curve of an object comprising an EVA matrix, left in an oven at 38° C.

Figure 6:
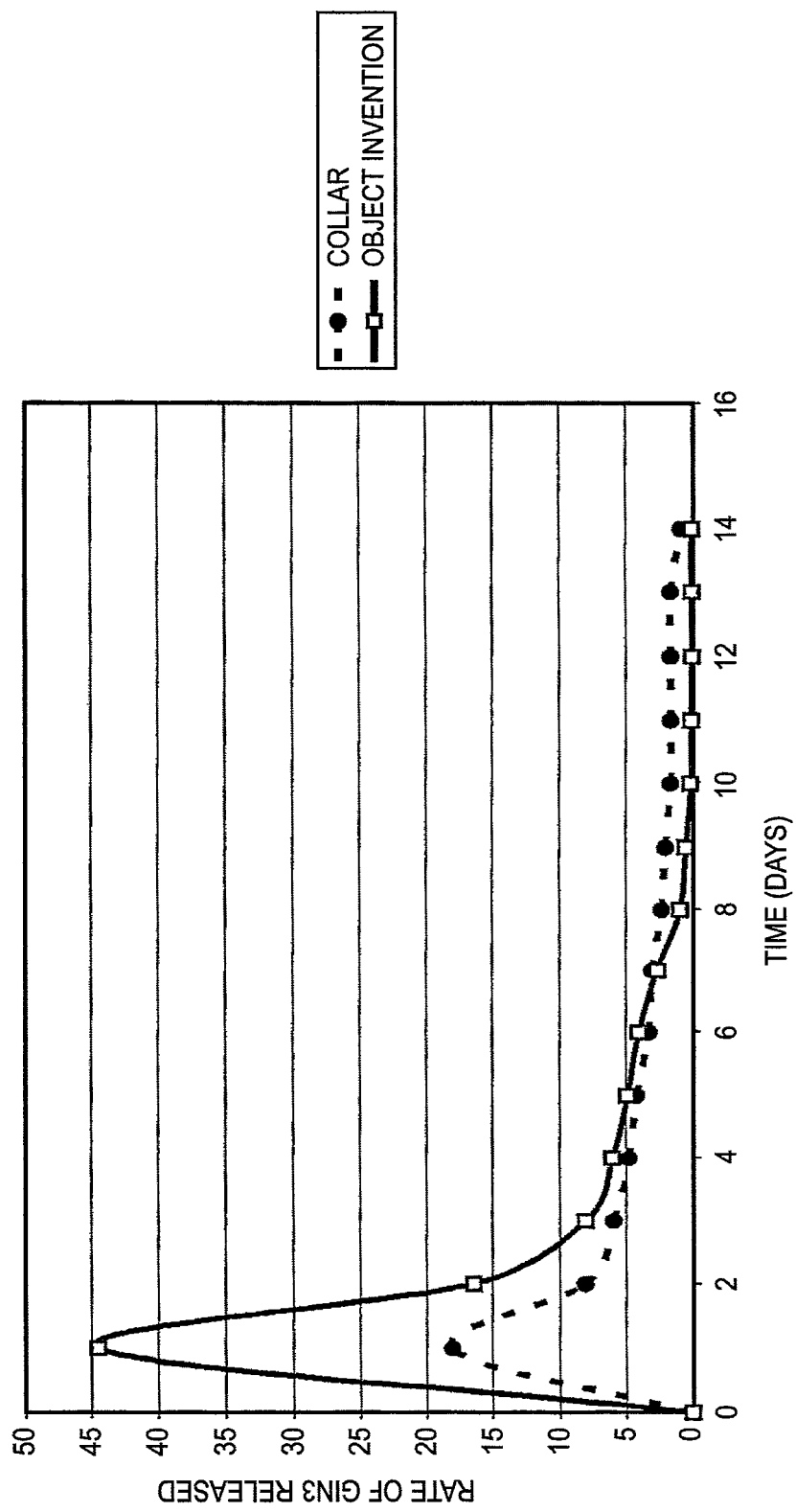

FIG. 6 represents the comparative curves of the release kinetics at 38° C. of an antiparasitic PVC collar and an object comprising an EVA matrix, both charged with GIN3.

Figure 7:
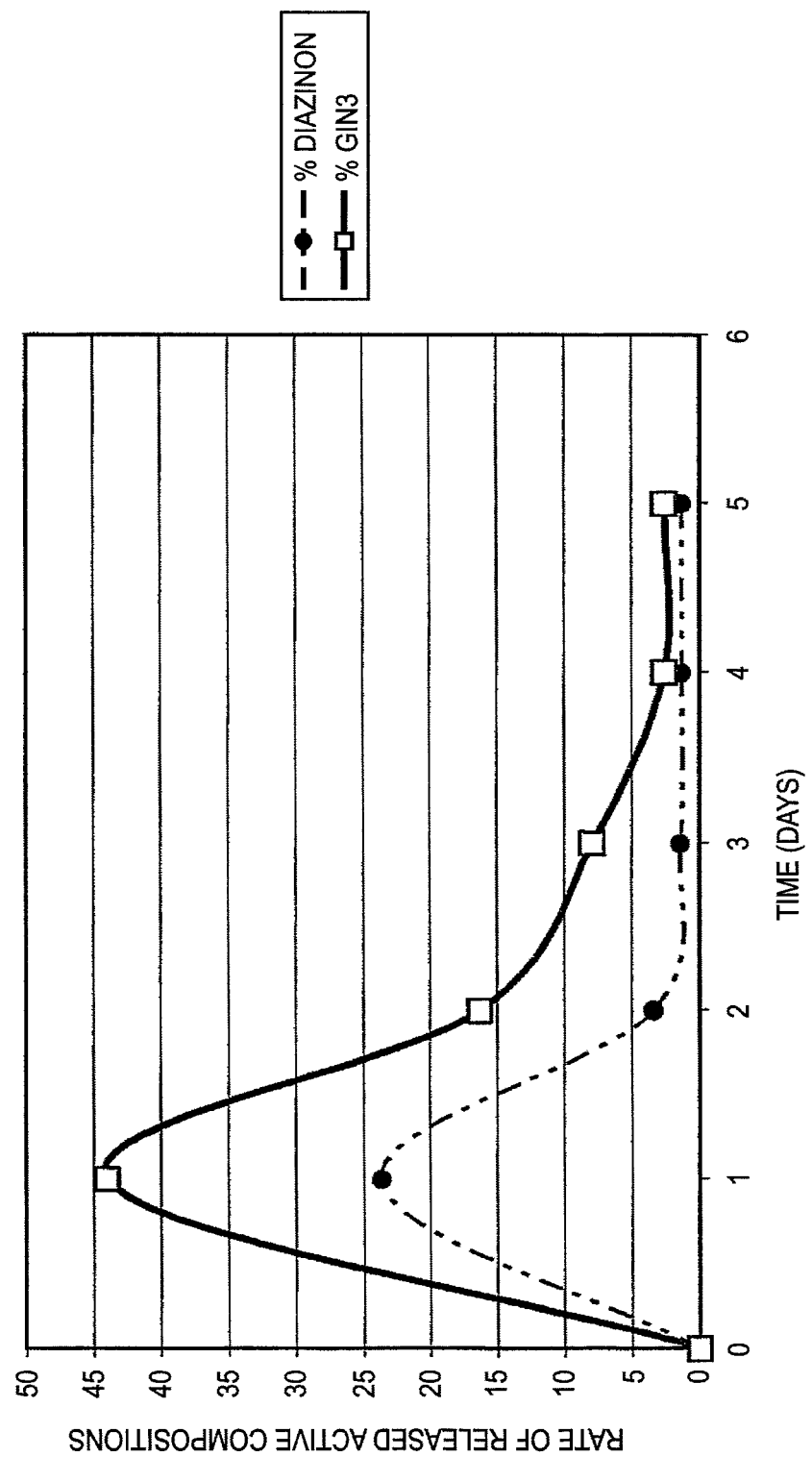

FIG. 7 represents the comparative curves of the release kinetics of GIN3 and DIAZINON incorporated in an EVA matrix.

Figure 8:
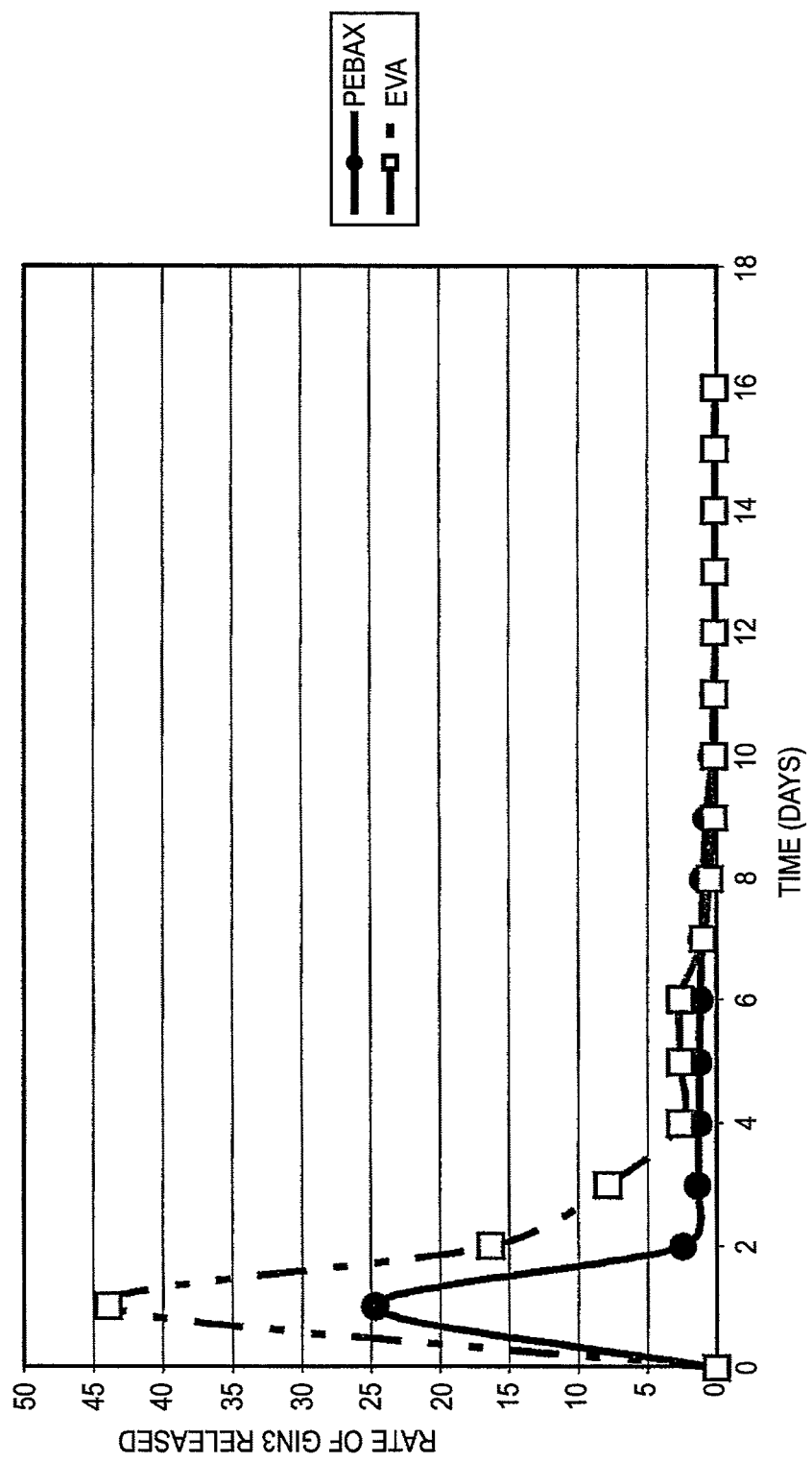

FIG. 8 represents the comparative curves of the release kinetics of GIN3 incorporated in an EVA matrix and in a PEBAX matrix for the object of the invention.

Figure 9:
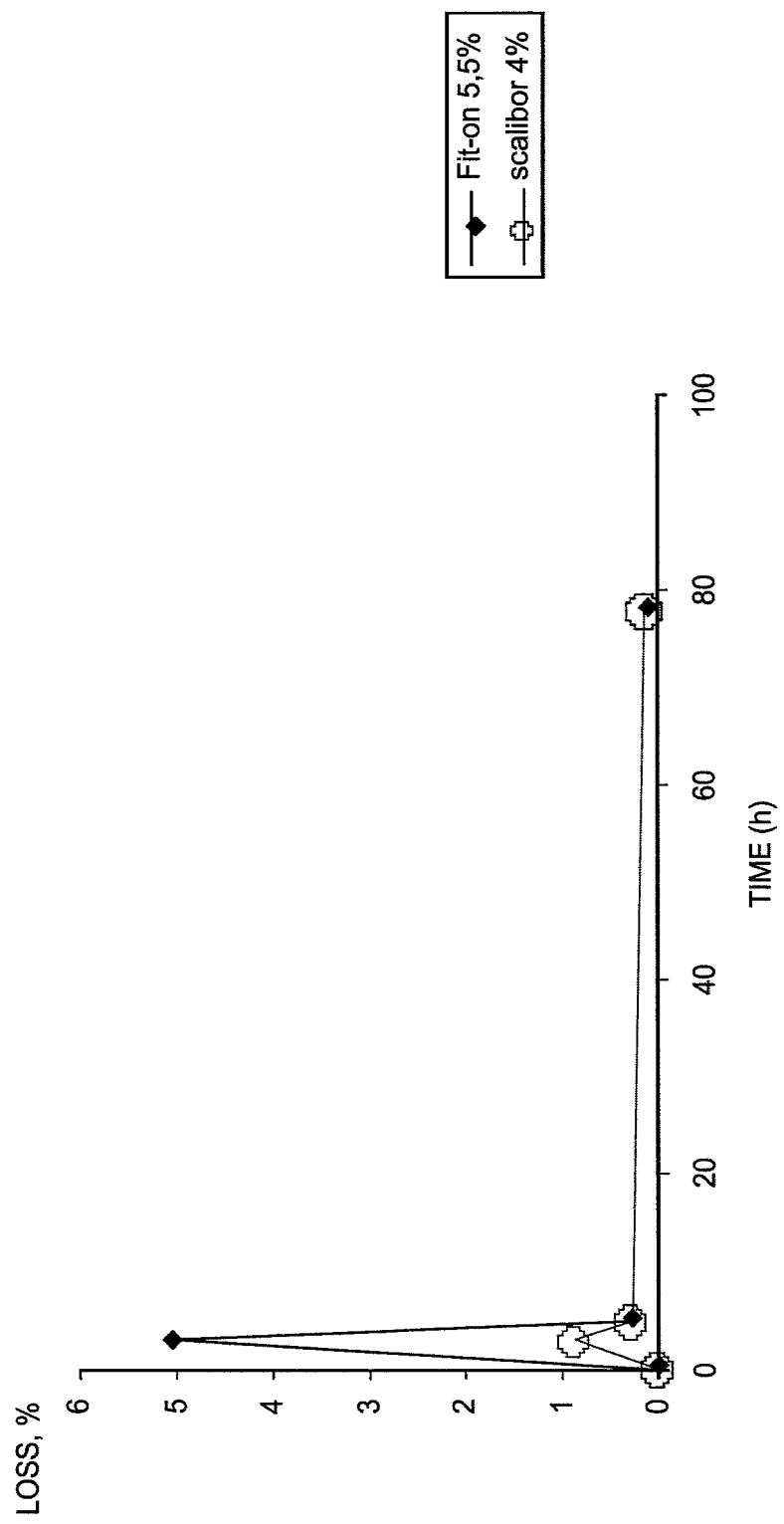

FIG. 9 represents the comparative curves of the release kinetics of deltamethrin used as active composition incorporated in an EVA/PEBAX matrix and a PVC matrix.

Figure 10:
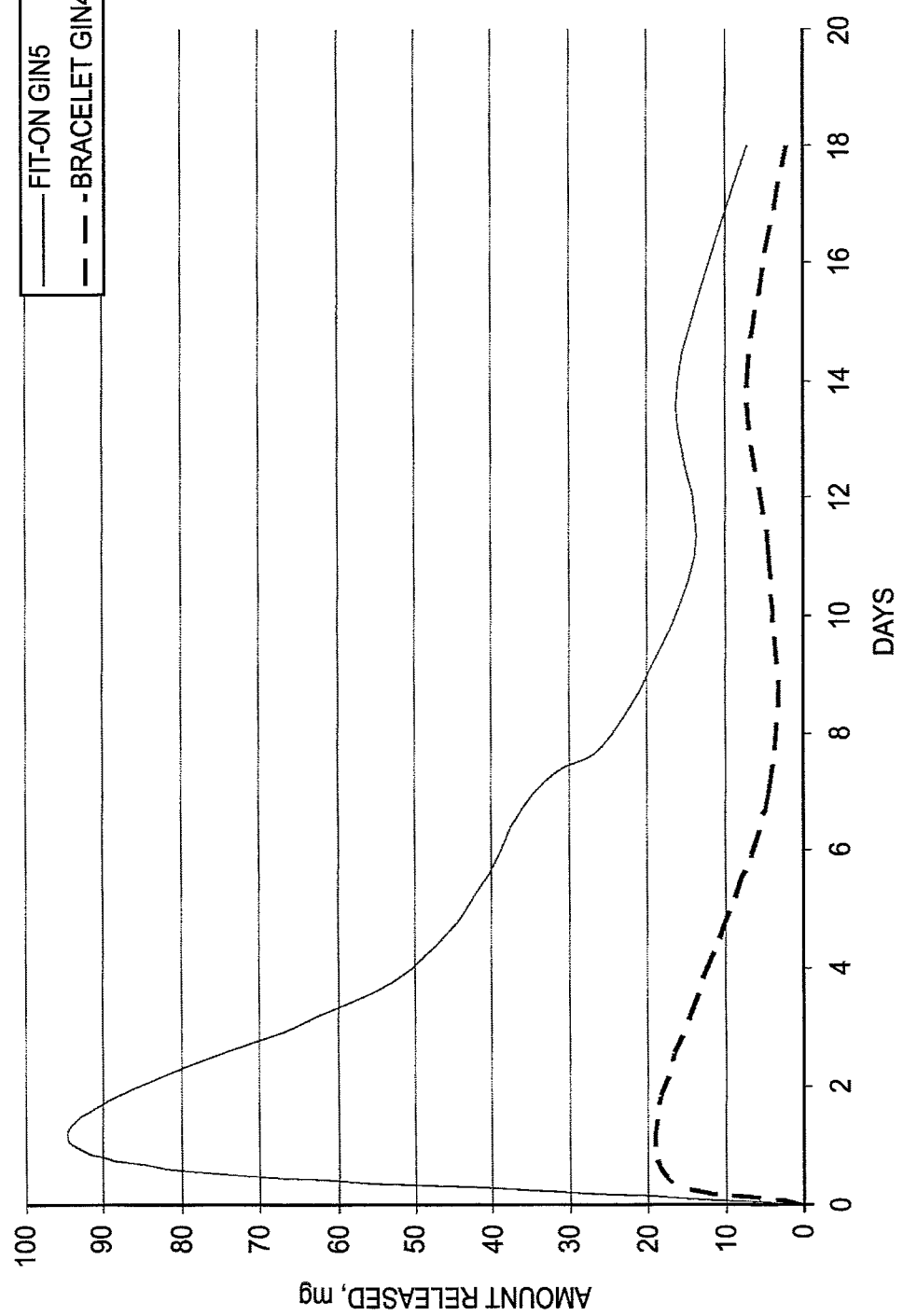

FIG. 10 represents the comparative curves of the release kinetics of an EVA/PEBAX matrix according to the invention charged with a complex active composition such as GIN5, and a PVC matrix charged with another complex active composition, GIN4.

Figure 11:
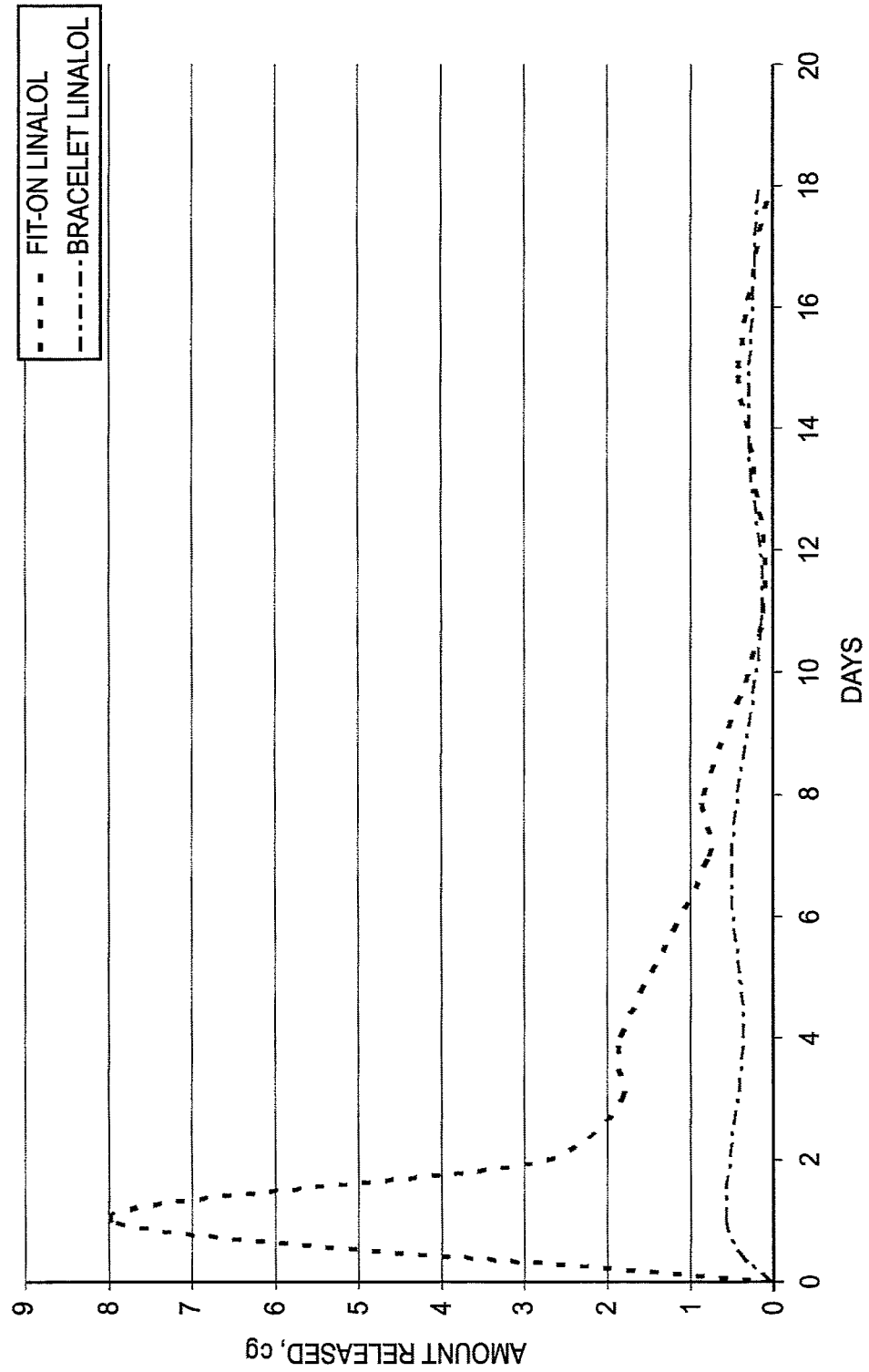

FIG. 11 represents the comparative curves of the release kinetics of linalol in an EVA/PEBAX matrix according to the invention and a PVC matrix.

In a specific embodiment of the invention, preferably an ethylene/vinyl acetate (EVA) copolymer with a vinyl acetate (VA) content ranging between 15 and 33% by weight, preferably 20% by weight, in relation to the weight of the ethylene/vinyl acetate copolymer, with a glass transition temperature (Tg) ranging between 50 and 70° C., preferably 58° C., and a melting point at 80° C., is used as carrier polymer to the advantage of the invention. This copolymer is combined with a PEBAX, or Polyether Block Amide (PEBA), constituted of a linear and regular sequence of flexible polyether (PE) segments and polyamide (PA) segments of PEBAX MX 1717 grade, of the type marketed by ARKEMA, with a Vicat point of 60° C. By way of comparison, the polyvinyl chloride (PVC) used in flexible form is LACOVYL® SK 70 marketed by ARKEMA, the glass transition temperature (Tg) of which is 85° C. and the melting temperature 130° C. PVC decomposes at 180° C. in 2 minutes and already at 100° C. in 1 h. To do this, it requires many technological additives to prevent and avoid both its toxicity and its instability by thermal decomposition. The use of plasticizers such as phthalates is necessary for its forming by injection or by extrusion.

Among the natural antiparasitic ingredients that are used according to the invention may be mentioned GIN preparations comprising a synergic mixture of terpenic alcohols, essential oils and non active oil [French patent application No. 06/08554 filed on Sep. 29, 2006], those based on plant extracts still authorized by the European Directive on biocides, 98/8/EC.

Other antiparasitic agents, known as synthetic antiparasitic agents, have been used according to the invention, namely: chlorpyrifos, diazinon, pyrethrinoids such as deltamethrin, etc.

The incorporation of an active ingredient in a polymer matrix so that it may release said active ingredient over time and in certain conditions makes said matrix an active polymer. According to the invention, the active polymer is composed of an EVA/PEBAX matrix, in which an antiparasitic agent is incorporated, which is specifically delivered by the matrix onto the skin or the hair coat.

The examples given hereafter to illustrate the invention are not exhaustive and in no way limit the scope of the present application and the alternative applications ensuing thereof.

EXAMPLE 1

Manufacture of a Specific Device Comprising an EVA Matrix

The forming of the object of the invention involves several steps already detailed in the French patent application No. 06/04455 filed on May 18, 2006, also allowing to obtain an matrix made of EVA only, namely:

for this example it was chosen to work with an ethylene/vinyl acetate (EVA) copolymer matrix. It was chosen to blend two grades of EVA, namely: ALCUDIA® PA-541 EVA comprising 20% vinyl acetate and PA-440 comprising 28% vinyl acetate, from REPSOL YPF, in a 57/43 ratio;

the antiparasitic composition chosen is GIN3 produced by AB7 Industries (composed of tea tree oil, geraniol, lavendula burnatii (or "lavendin") oil, grapefruit oil, mint oil, castor oil, coconut oil, sodium citrate solution);

first, GIN3 is incorporated in the granules of EVA using a rapid mixer [French patent application n° 06/04457 filed on May 18, 2006] with a ratio of 30% of GIN3 to 70% of EVA;

the granules thereby charged are treated in a 1.35 T ARBOURG 221M350-75 injection molding press, according to the following temperature chart: 70° C.—80° C.—90° C.—120° C., and the mold is programmed at 40° C.;

the "fit-on" objects obtained according to the invention (FIG. 1) are medallions of 35 mm Ø, of 2.5 mm thickness, weighing 3 grams, which are divided into three lots:
one lot intended for the in vitro tests
one lot intended for the in vivo tests
one lot intended for the kinetics study.

EXAMPLE 2

Diffusion Test of Several Active Principles in an EVA Matrix

Aim of the Test and General Principles

It is accepted that, in active polymers, the stored active composition migrates to the surface of the polymer. Once the surface has been reached, in real use, either the active ingredients (or a part thereof) evaporate, or they solubilize in the cutaneous sebum (case of use as collar or patch).

It is also noted that an accumulation of active ingredient at the surface considerably hinders the migration of said active ingredient from the core of the matrix to the surface.

Starting from the hypothesis that only the active ingredient migrates, the general release kinetics of the active ingredient is thus the component of the rate of migration of the active ingredient in the matrix and its elimination, by evaporation and/or by solubilization, from the surface of the object. The resulting kinetics is, at a given moment, limited by the slowest of these phenomena.

The test below aims at studying the kinetics by limiting the elimination of the active ingredient to its solubilization in a lipid. To that end, the experimental device is designed to limit evaporation phenomena.

Experimental Equipment a) Samples

Figure 1:
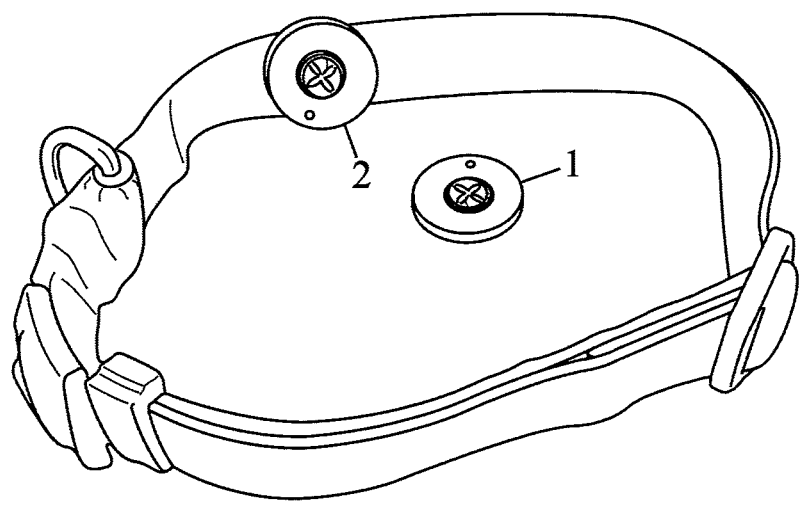
FIG. 1 represents the device object of the invention, a fit-on, used during the tests described hereafter, alone (1) and fitted on a collar (2) for the in vivo tests.

It is necessary that the samples have a comparable weight and surface area. It is proposed to use samples molded in the "medal" mold, producing discs of 35 mm Ø and 2.5 mm thickness (FIG. 1). On one face of this mold are engraved the initials MI. The mold is also provided with a peripheral hole of 2.5 mm Ø. It is accepted that these samples will always be used with the engraved face (by convention, the top face) upwards.

b) Supports

The samples will be placed in a Petri dish with the bottom face against a layer of absorbent material soaked with a fatty substance (olive oil). The absorbent material is comprised of a layer of non-woven fabric or of an absorbent paper of the filter paper type. This solution is adopted so that the sample rests on a solid support enabling a permanent contact of the surface (bottom face) with the oil, without however the whole sample being soaked therein. At the end of its migration to the surface, the active composition, which is liposoluble, is dissolved in the oil, thereby simulating the suint of the animal. The amount of fatty substance introduced is identical from one dish to the next.

Protocol

The samples tested comprise a PA-541 (57%) and PA-440 (43%) EVA matrix in which are incorporated, depending on the case, two different active ingredients:
one sample with GIN2, composed of β-citronellol, nerol, geraniol, tetrahydrogeraniol, coconut and castor oil;
and one sample with GIN3, composed of geraniol, 1-terpinene-4-ol, γ-terpinene, α-terpinene, α-terpinolene, 1,8-cineole, α-pinene, α-terpineol, symene, aromadendrine and d-limonene. The active compositions are each present in the two respective matrices with a 15% ratio.

The samples of each GIN2/Matrix and GIN3/Matrix pair are weighed exactly, then each is introduced in a test dish that is covered with a lid.

Samples are collected every 24 hours, wiped with absorbent paper, then weighed to determine the amounts of active ingredients migrated into the oil. The test is carried on for the time necessary for a significant depletion of the samples in active ingredients. At the end of the test, an extraction may be carried out on the oil of the soaked dishes in order to validate the results of the weighings (reconciliations).

The results obtained clearly demonstrate that the active ingredients incorporated in the matrix migrate well into the lipidic medium according to a reproducible regime (Table 1), whatever the antiparasitic composition used (here for example GIN2 based on terpenic alcohols and GIN3 based on plant extracts).

TABLE 1

Different constituents assayed in the olive oil contained in the non-woven fabric (extraction support) after the test time.

| A: GIN3 | | | | | |
|---|---|---|---|---|---|
| ACTIVE INGREDIENTS | α-terpinene | linalol | linalyl acetate | 1-terpinene-4-ol | geraniol |
| GIN3 | 91.6 | 62.7 | 74.6 | 63.7 | 56.5 |
| B: GIN2 | | | | | |
| ACTIVE INGREDIENTS | tetrahydro-geraniol | β-citronellol | nerol | geraniol | |
| GIN2 | 74.2 | 71.4 | 73.9 | 71.9 | |

Percentages in relation to the initial amounts contained in the matrix of the sample with an EVA matrix.

Figure 2:
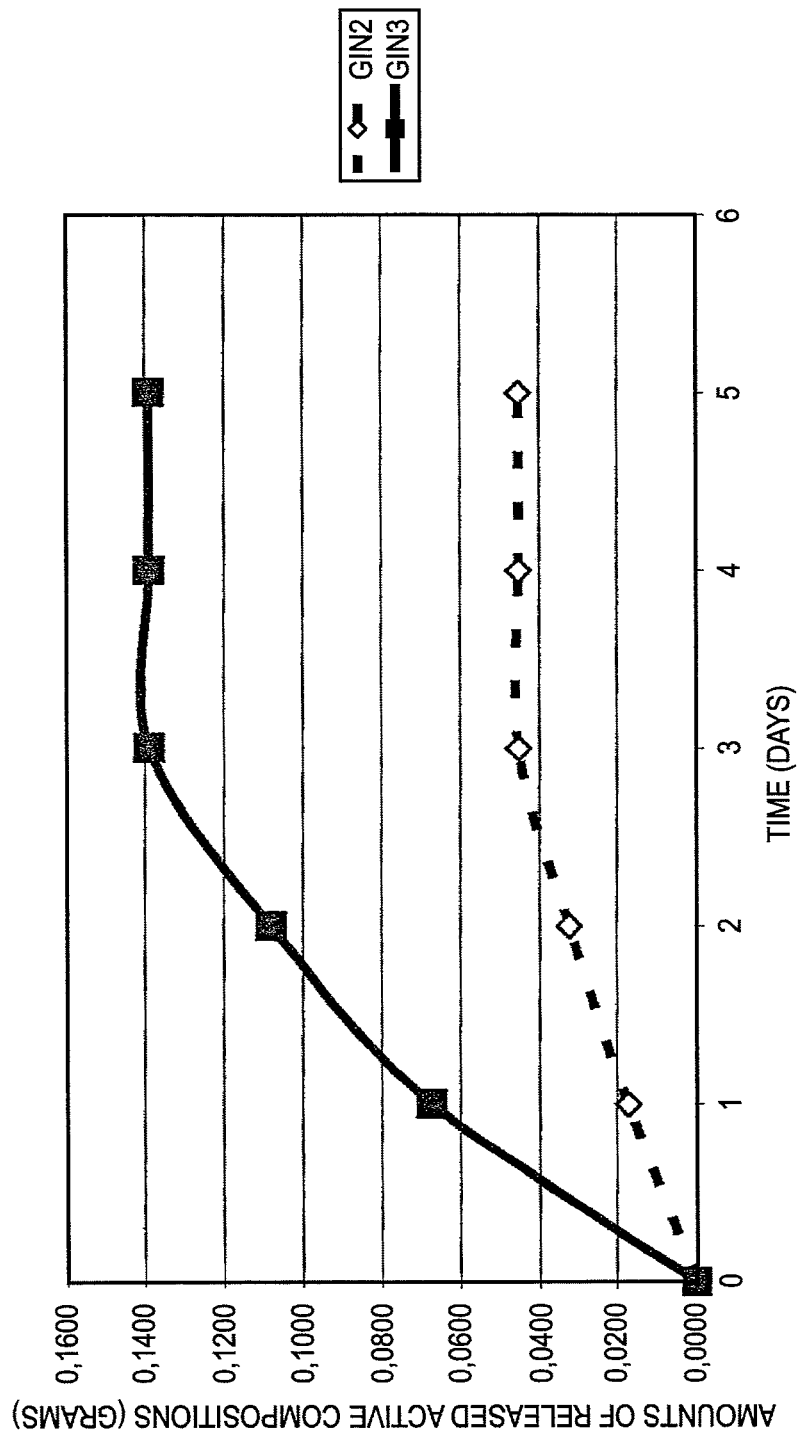
FIG. 2 represents the comparative curves of the operation under in vitro conditions of objects composed of an EVA matrix, impregnated with two different active compositions, GIN2 and GIN3, the compositions of which are defined hereafter.

The profile of the release curves, based on the weight loss from the objects, which represents the overall loss of active composition by considering the matrix stable, established from daily weighings (FIG. 2), makes it possible to visualize precisely the impact of the antiparasitic ingredient in spot-on mode the first three days, and in support of this spot-on impact the following days. The spot-on impact of GIN3 is more intense than GIN2 for the same matrix. This operation characteristic is used by the invention; the fit-on makes it possible to better target the antiparasitic ingredients to be used.

EXAMPLE 3

Diffusion Test of a Composition in an EVA Matrix vs. a PVC Matrix

The protocol of example 2 is repeated with, this time, one single composition but two different matrices, namely:
a PA-541 (57%) and PA-440 (43%) EVA matrix for a first group of samples,
a PVC matrix as reference for a second group of samples.

The comparison between the two matrices, EVA and PVC (FIG. 3), may easily be made by noting that for the same active antiparasitic ingredient, in this case GIN3, the spot-on impact obtained with the EVA matrix is markedly more intense than that obtained with PVC.

EXAMPLE 4 in vivo Diffusion Test of a Composition in an EVA Matrix vs. a PVC Matrix

The in vivo tests allow to validate, on a representative example, the practical use of an EVA matrix.

The principle of this experiment consists in assaying the amount of active ingredient released in real conditions, the sample being applied to an animal.

The test uses the same elements as in examples 2 and 3. Said elements are secured to a fabric collar by means of an attachment device that can easily be removed. The collar is placed on the neck of a batch of dogs of comparable format and hair coat type and kenneled in a similar manner, so as to limit the test variables.

Protocol

For this test, two types of samples with GIN3 were used: one sample on EVA polymer of about 2.0 g, with 15% of active ingredient, and one sample on PVC base of about 3.0 g, with 13.5% of active ingredient. These samples are exactly weighed then assembled as above and placed on adult male German shepherd dogs.

The date and the time of application are accurately noted. At regular intervals, the collars are removed from the necks of the dogs, the sample is disassembled, cleaned with absorbent paper imbibed with alcohol and then accurately weighed.

The results are expressed in weight loss and thus as active ingredient released as a function of time.

Results

The results obtained (FIG. 4) confirm the kinetic profiles obtained in vitro. In the first twenty hours, an average release rate of the order of 2 mg/hour is observed, which then drops to a steady value of about 0.75 mg/hour. The therapeutic dose is estimated at 50 mg/m$^2$ of surface area, i.e. for dogs of this size (0.8 m$^2$), 40 mg of active ingredient released. It may be seen that despite the small size of the device with an EVA matrix, the therapeutic dose is reached from the twentieth hour. The release rate, after 50 hours, is 18 mg/day. This value is to be compared to the degradation rate of the active ingredient on the animal. According to the measurements made with concentrated liquid forms, the loss of active ingredient is estimated at 8 mg/day. It may be seen that this loss of active ingredient by degradation and by evaporation is easily compensated by the amount of active ingredient released by the device provided with an EVA matrix.

EXAMPLE 5 in vivo Diffusion Test of a Composition in an EVA Matrix

The monitoring of the kinetics study was carried out by approaching the temperature conditions of the animals, namely 38° C., and thereby creating appreciation elements obtained exactly without the chance factors of variables, which are factors that can influence the operating state of the object of the invention.

The monitoring of the kinetics study consists in placing an object comprising an EVA matrix in operating conditions and measuring by weighing the amounts of antiparasitic ingredients released on a daily basis.

The matrix retained for this example is EVA, whereas the antiparasitic ingredient used is GIN3, charged with a rate of 30%.

The results obtained (FIG. 5) confirm those already described in example 2. Indeed, as of the first day, the EVA object releases 45% of the GIN3 incorporated, dropping to 18% the second day and 7% the third day. The spot-on effect is thus obtained over the first three days with 70% of antiparasitic ingredient. The period of support of the spot-on impact is ensured with 28% of antiparasitic ingredient delivered over a period at least equal to the period of remanence of "spot-on" type concentrated solutions, given the storage capacity of the adipose tissue, which allows to obtain an efficacy that largely exceeds the apparent release time (7 days).

Since the aim in this case was to do at least as well as the concentrated liquid "spot-on" from the therapeutic point of view, but without the drawbacks linked to this form of treatment, the EVA object completely fulfils its function. The losses of active ingredient by oxidative degradation and by evaporation are eliminated, as are the risks of undesirable contact with the product for a child or another animal and even the animal itself. The amount of active ingredient administered is optimized, which avoids any risk of overdosing.

EXAMPLE 6

Comparative Test of an EVA Device with a PVC Antiparasitic Collar

The therapeutic advantage of an object comprising an EVA matrix over a conventional antiparasitic collar is easily demonstrated in this example.

The object comprising an EVA matrix is compared to a conventional Répul'7 collar composed of a PVC SK70 matrix to which has been added a plasticizer and other forming additives. The two objects compared are charged with the same antiparasitic ingredient, namely GIN3, and are put under operating conditions for 14 days: 38° C. in a ventilated oven. The samples are weighed every 24 hours. At the end of this period, 1 g samples are taken on each object from the different lots subjected to the test in order to analyze qualitatively and quantitatively the remanent active ingredient. The antiparasitic ingredient is extracted thereof and assayed by gas phase chromatography (GPC).

The results obtained (FIG. 6) show that the EVA object has released 89 mg/d, i.e. 10% of the GIN3 incorporated, and the conventional collar only 34 mg/d, i.e. 0.7% of the GIN3 incorporated. Indeed, the EVA object weighs 3 grams and contains 900 mg of GIN3 whereas the collar weighs 30 grams and contains 4500 mg of GIN3.

Monitoring the release kinetics of these two types of object allows to highlight an operating difference, in the sense that:
  the EVA object releases up to four times more antiparasitic ingredient the first three days than the collar, depending on the antiparasitic ingredient incorporated,
  over the following seven days, the EVA object loses its antiparasitic ingredient more intensely up to depletion, whereas the collar releases less of it and tends towards a regularity that can last another 27 days.

The EVA object thus delivers, in a short time, an efficacious amount of antiparasitic active ingredient, enabling a "knockdown" effect for the same reasons as "spot-on" type concentrated solutions, but without the drawbacks of the latter.

Indeed, unlike concentrated solutions, in the case of an EVA object, only the therapeutic dose is released and not the totality of the dose. This limits the risks of overdosing and the toxic risks linked to accidental contact with the active ingredients by the animal itself, another animal in its circle, or even its masters.

The active ingredients not released remain shielded from degradations and evaporation. This limits the losses and make it possible to reduce the necessary doses of active ingredients or to extend the efficacy. The remaining product is then released progressively at a slower rhythm and compensates the losses due to evaporation and degradation of the active ingredient. By this means, the therapeutic dose is maintained longer than in the case of "spot-on" type concentrated solutions, where the totality of the dose is subjected at the same time to evaporation and degradation.

Compared to the conventional antiparasitic collar, which is intended for preventive treatment of long duration, the EVA object has the advantage of providing a therapeutic knockdown action. The two objects may moreover be used in a complementary manner, the conventional antiparasitic collar relaying the action of the EVA object.

EXAMPLE 7

Diffusion Test of an EVA Device Comprising Several Active Compositions in a Same Matrix In a specific embodiment, the present invention comprises two or more antiparasitic active ingredients with complementary effects and different kinetics. To illustrate this aspect of the invention, it was decided to compare GIN3, incorporated in the EVA already presented in example 5, and DIAZINON, also incorporated in the EVA according to the same conditions, namely forming the object according to the steps already detailed in French patent application n° 06/04455 filed on May 18, 2006 cited in example 1:

- it was chosen for this example to work with an ethylene/vinyl acetate (EVA) copolymer matrix. It was chosen to blend two grades of EVA, namely: ALCUDIA® PA-541 EVA comprising 20% vinyl acetate and PA-440 comprising 28% vinyl acetate, from REPSOL YPF, in a 57/43 ratio;
- the antiparasitic ingredients chosen are DIAZINON and GIN3;
- first, the DIAZINON is incorporated in the granules of EVA by means of a rapid mixer [French patent application n° 06/04457 filed on May 18, 2006] with a ratio of 30% of DIAZINON to 70% of EVA;
- secondly, GIN3 is incorporated in the granules of EVA by means of the same rapid mixer already cited with a ratio of 30% of GIN3 to 70% of EVA;
- then the granules with DIAZINON are blended with the granules charged with GIN3 in a 40/60 ratio;
- the granules thus blended are processed in a 1.35 T ARBOURG 221M350-75 injection molding press, according to the following temperature chart: 70° C.,—80° C.—90° C.—120° C., and the mold is programmed at 40° C.;
- the EVA objects obtained (FIG. 1) are medallions of 35 mm Ø, 2.5 mm thickness, weighing 3 grams, and are divided into three lots:
  - one lot intended for the in vitro tests
  - one lot intended for the in vivo tests
  - one lot intended for the kinetics study.

It follows that the release behavior of the two active compositions is not the same (FIG. 7). Indeed, DIAZINON happens to be released in smaller amount the first three days, i.e. 28%, compared to 68% of GIN3 for the same period, stabilizing out as of the fourth day at 1.30% per day for the remaining 70%, whereas GIN3 is going to run out very quickly, since 80% of it will be released in 12 days.

DIAZINON is a much heavier molecule than GIN3 which is, moreover, highly volatile. Its intra-matricial transfer is thus slower, which gives lower amounts of antiparasitic agents made available.

The antiparasitic activity of DIAZINON is going to extend the activity of GIN3, which will have stopped, knowing that the two compositions have different modes of action, with DIAZINON being an organophosphorous compound, and GIN3 acting both as an organochlorine and as an organophosphorous compound.

Two compositions with different effects and actions may thus be incorporated in a same matrix to obtain a complementary operation with combined effects.

EXAMPLE 8

Diffusion Test of a Device Comprising a Matrix Composed of Several Different Polymers The object of the invention offers the advantage of a modulated operation by combining in its matrix two polymers:

1) "Polyether Block Amides" or PEBAX®, marketed by ARKEMA, have the advantage of having a low glass transition temperature (Tg) of 60° C., but a melting point ranging between 130 and 170° C. PEBAX® decomposes between 300 and 350° C.
2) It was chosen for this case to work with a mixture of two grades of ethylene/vinyl acetate (EVA) copolymer namely: ALCUDIA® PA-541 EVA comprising 20% vinyl acetate and PA-440 comprising 28% vinyl acetate, from REPSOL YPF, in a 57/43 ratio. EVA has a glass transition temperature (Tg) of about 60° C. and a melting point of 84° C., for a decomposition temperature above 200° C.

Due to their differences from the point of view of characteristics, the PEBAX and the EVA are charged separately with active compositions, with a ratio of 25% of GIN3 in the EVA and 37.5% of GIN3 in the PEBAX, as already described in the preceding examples. It is then proceeded as follows:

- the granules charged with GIN3 are mixed in a ratio of 60% of EVA to 40% of PEBAX;
- the mixed granules of EVA and PEBAX thereby charged are processed in a 1.35 T ARBOURG 221M350-75 injection molding press, according to the following temperature chart: 70° C.—80° C.—110° C.—140° C., and the mold is programmed at 40° C.;
- the "fit-on" objects obtained (FIG. 1) are medallions of 35 mm Ø, 2.5 mm thickness, weighing 3 grams, and are divided into three lots:
  - one lot intended for the in vitro tests
  - one lot intended for the in vivo tests
  - one lot intended for the kinetics study.

The GIN3 release studies carried out separately beforehand on the two polymers (FIG. 8) show that the EVA releases 73% of GIN3 in 4 days whereas the PEBAX only releases 31%. In the end, the EVA releases almost all of the active ingredient incorporated, whereas the PEBAX continues to release small amounts for even longer.

The combination of the two polymers contributes to combining in a synergic manner the two actions, which are:

- a large amount of active ingredients released for the knockdown effect over the first days provided by the EVA,
- a small amount of active ingredients regularly released for the upkeep effect of longer duration provided by the PEBAX.

Two therapeutic effects may thus be obtained with a same active composition, by acting on the composition of the matrix, particularly by combining a polymer with rapid action (e.g.: EVA) and another with slow action (e.g.: PEBAX) with a ratio ranging from 90 to 50% for EVA, preferably 60% by weight.

The operation may be carried out in the same way but with two or more different active compositions affording a different mode of action, so as to obtain a therapeutic effect that is the result of the combined effects of the different active compositions.

EXAMPLE 9

Diffusion Test of a Device Comprising a Matrix Composed of Several Different Polymers Compared to the Diffusion Test of a Commercially Available Collar The object of the invention is formed identically to example 8 in which the GIN3 is replaced by 98% minimum technical grade Deltamethrin, from VETPHARMA, in the final ratio of 5.5% of Deltamethrin to 94.5% of composed matrix. The distribution of the Deltamethrin in the different constituents of the matrix is as follows:
  60% of EVA with 4.58% of Deltamethrin
  40% of PEBAX with 6.88% of Deltamethrin The commercially available collar chosen is SCALIBOR with 4% of Deltamethrin to 96% of PVC matrix.

Protocol:

The diffusion is observed in vitro in an accelerated manner as follows:
  Taking 5 g of sample with 3 repetitions for each object (object of the invention and collar to be compared), which represents 200 mg of Deltamethrin for the collar and 275 mg for the object of the invention.
  Diffusing each sample in a beaker containing 50 ml of olive oil under continuous agitation.
  Sampling of oil at T0, T3, T5, T72 (hours) to assay the amount of Deltamethrin released.
  Assaying by extraction the Deltamethrin in the samples at T0 and at T72 to confirm the amounts released.

Results:

The results presented graphically in FIG. 9 show that, at the beginning of the application, the object of the invention has a release peak of Deltamethrin 9 times higher in absolute value than the SCALIBOR collar, viz. for the first three hours 1.58 mg of Deltamethrin are released by the sample of the collar compared to 14.3 mg by the sample of the object of the invention.

It has been parallely observed in vivo that the SCALIBOR collar only begins to be effective about 48 hours after its application, much later than the object of the invention, the efficacy of which is observed 4 hours only after its application.

Moreover, the second polymer, i.e. PEBAX, properly plays its role of upkeep reservoir in so far as it prevents a sudden emptying of Deltamethrin from the object of the invention, as would happen with a matrix of EVA only. The release even becomes equivalent to that of the collar used for comparison.

The advantage of the object of the invention over the collar used for comparison is thus established in this example, as well as the role played by each of the polymers composing its matrix.

EXAMPLE 10

Diffusion Test of a Device According to the Invention Comprising the GIN5 Insect Repellent in a Matrix Composed of Several Different Polymers Compared to the Diffusion Test of a Bracelet with GIN4

The bracelet chosen is a product from AB7 INDUSTRIES charged with 15% of GIN4 in 85% of PVC matrix. GIN4 is an insect repellent from AB7 INDUSTRIES based on geraniol, linalol, peppermint oil, basil oil, coconut oil, citric acid, fragrances of mulberry and lychee.

The object of the invention is formed in an identical manner to example 8, with GIN3 being replaced by GIN5, from AB7 INDUSTRIES, in the final ratio of 20% of GIN5 to 80% of composed matrix. GIN5 is an improved formula of GIN4 to favor the rate of release while at the same time reducing the risk of toxicity that could be due to a too high amount of active ingredient released over a very short time lapse. The distribution of GIN5 in the different constituents of the matrix is as follows:
  60% of EVA with 17% of GIN5
  40% of PEBAX with 25% of GIN5.

Protocol:

The diffusion is observed in vitro by kinetic monitoring of the release of the active ingredient (which is volatile) by introducing the samples in an oven at 38° C. The samples are weighed every day to determine the amount of active ingredient lost thereof.

Results:

The results presented graphically in FIG. 10 show that the object of the invention has a GIN5 release peak from the beginning of the application four times higher in absolute value than that of the bracelet with GIN4.

The formulation of the active ingredient and that of the matrix obviously have a considerable influence on the operation of these two objects, if account is taken of the fact that the levels of active ingredients incorporated in the matrices are not so different, with 15% in the case of the bracelet and 20% in the case of the object of the invention.

The advantage of the object of the invention over the bracelet is evident and largely justifies its interest.

EXAMPLE 11

Diffusion Test of a Device According to the Invention Comprising the Active Ingredient LINALOL in a Matrix Composed of Several Different Polymers Compared to the Diffusion Test of a Bracelet with LINALOL The bracelet chosen is a product from AB7 INDUSTRIES charged with 15% of LINALOL in 85% of PVC matrix. LINALOL is one of the main constituents of GIN4, the insect repellent of AB7 INDUSTRIES.

The object of the invention is formed in an identical manner to example 10, the GIN5 being replaced by LINALOL, in the final proportions of 30% of LINALOL to 70% of composed matrix. The distribution of LINALOL in the different constituents of the matrix is as follows:
  60% of EVA with 25% of LINALOL
  40% of PEBAX with 37.5% of LINALOL.

Protocol:

The diffusion is observed in vitro by kinetic monitoring of the release of the active ingredient (which is volatile) by placing the samples in an oven at 38° C. The samples are weighed daily to determine the amount of active ingredient lost.

Results:

The results presented graphically in FIG. 11 show that the object of the invention has a peak of release of LINALOL from the start of the application 16 times higher in absolute value than that of the bracelet.

This enormous difference confirms the efficacy results observed in the preceding example and in vivo.

The advantage of the object of the invention over the bracelet is provided here by the combination of the composition of the matrix and the concentration of the active ingredient.

The object of the invention is thus adaptable to the active ingredient and to the requisite level of action. As a result, the latter may be dosed as a function of demand.

What is claimed is:

1. Device for storing and releasing one or more mixed active compositions for controlling the external parasites of domestic animals, insects and other living organisms, wherein it is composed of a polymer matrix comprising a mixture of an ethylene/vinyl acetate copolymer blended with a polyether block amide, said polymer matrix being charged according to an active composition/matrix weight ratio below 0.66, thereby providing both a knockdown effect and a regular release of said active compositions.

2. Device according to claim 1, wherein the polymer matrix comprises one or more grades of ethylene/vinyl acetate with a vinyl acetate content ranging between 15 and 33% by weight in relation to ethylene/vinyl acetate.

3. Device according to claim 2, wherein the polymer matrix comprises two grades of ethylene/vinyl acetate, one comprising 20% by weight of vinyl acetate in relation to ethylene/vinyl acetate, the other comprising 28% by weight of vinyl acetate in relation to ethylene/vinyl acetate.

4. Device according to claim 1, wherein the ethylene/vinyl acetate copolymer has a glass transition temperature ranging between 50 and 70° C.

5. Device according to claim 4, wherein the ethylene/vinyl acetate copolymer has a glass transition temperature equal to 58° C.

6. Device according to claim 1, wherein the thickness of the matrix ranges between 2 and 10 mm.

7. Device according to claim 1, wherein the active composition(s) comprise natural antiparasitic ingredients and/or synthetic antiparasitic ingredients.

8. Device according to claim 7, wherein the natural antiparasitic ingredients comprise a synergic mixture of terpenic alcohols and/or essential oils and/or non active oils.

9. Device according to claim 7, wherein the synthetic antiparasitic ingredients comprise chlorpyrifos and/or diazinon and/or pyrethrinoids.

10. Device according to claim 1, wherein it is fitted on a collar, or any other support in contact with the animal, made of leather, fabric or plastic material.

11. Device according to claim 2, wherein the ethylene/vinyl acetate copolymer has a glass transition temperature ranging between 50 and 70° C.

12. Device according to claim 3, wherein the ethylene/vinyl acetate copolymer has a glass transition temperature ranging between 50 and 70° C.

13. Device according to claim 2, wherein the ethylene/vinyl acetate copolymer has a glass transition temperature equal to 58° C.

* * * * *